United States Patent [19]
McCarthy

[11] Patent Number: 5,158,549
[45] Date of Patent: Oct. 27, 1992

[54] SELF-LOCKING SINGLE-USE SYRINGE

[75] Inventor: Martin McCarthy, Milano, Italy

[73] Assignee: Vitrovivo Incorporated, Curacaco, Netherlands

[21] Appl. No.: 819,750

[22] Filed: Jan. 13, 1992

[30] Foreign Application Priority Data

Apr. 16, 1991 [IT] Italy .................................. 91000333

[51] Int. Cl.$^5$ .......................................... A61M 5/315
[52] U.S. Cl. ..................................... 604/110; 604/228
[58] Field of Search ............... 604/110, 198, 220, 228, 604/218

[56] References Cited

U.S. PATENT DOCUMENTS

| 4,915,692 | 4/1990 | Vierlier | 604/110 |
| 4,944,728 | 7/1990 | Carrell et al. | 604/110 |
| 4,994,034 | 2/1991 | Botich et al. | 604/110 |
| 4,994,044 | 2/1991 | Lo Duca | 604/110 |
| 4,995,869 | 2/1991 | McCarthy | 604/110 |
| 5,037,394 | 8/1991 | Marurik et al. | 604/110 |
| 5,057,087 | 10/1991 | Harmon | 604/110 |
| 5,066,277 | 11/1991 | Carroll et al. | 604/110 |

Primary Examiner—Paul J. Hirsch
Attorney, Agent, or Firm—Fulwider, Patton, Lee & Utecht

[57] ABSTRACT

Syringe of the type comprising a hollow cylindrical body 11 having a bottom closing part 14 bearing a connecting joint for a needle and in which there is arranged in a sliding manner a piston 12 driven by a stem 17 and fitted with a sleeve 13 sliding on the outside of said body 11. Said sleeve 13 is provided with first engagement means 26 designed to engage with said body 11 and prevent movement in one direction and second engagement means 25 designed to engage with the drive stem 17 of said piston 12 to similarly prevent movement in the other direction.

12 Claims, 2 Drawing Sheets

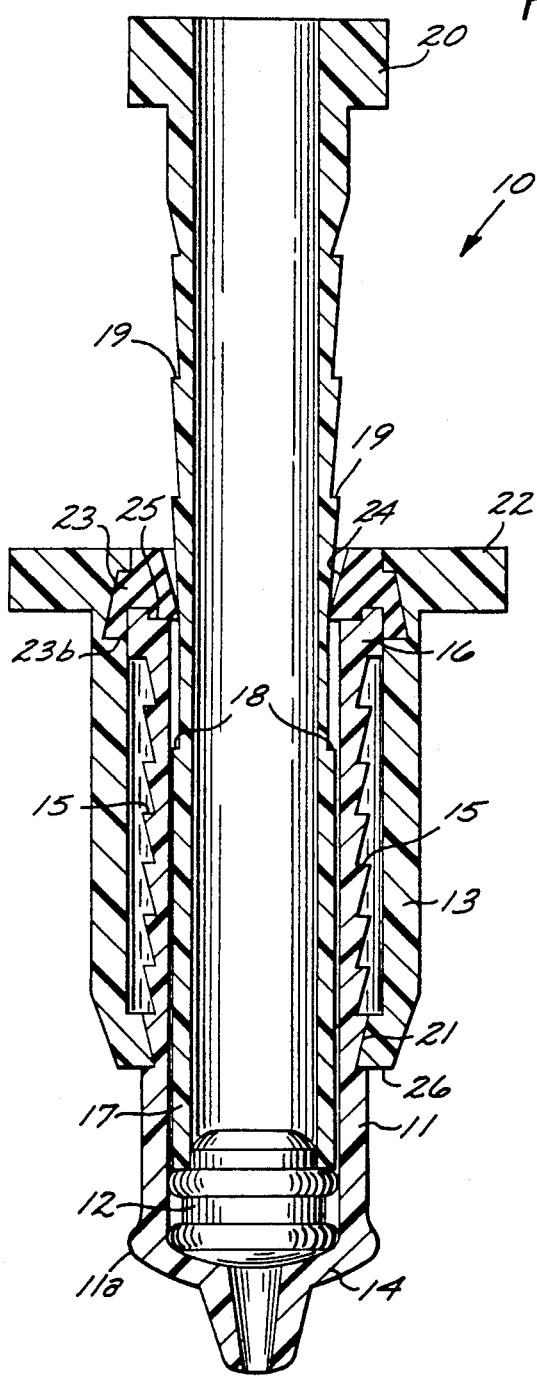
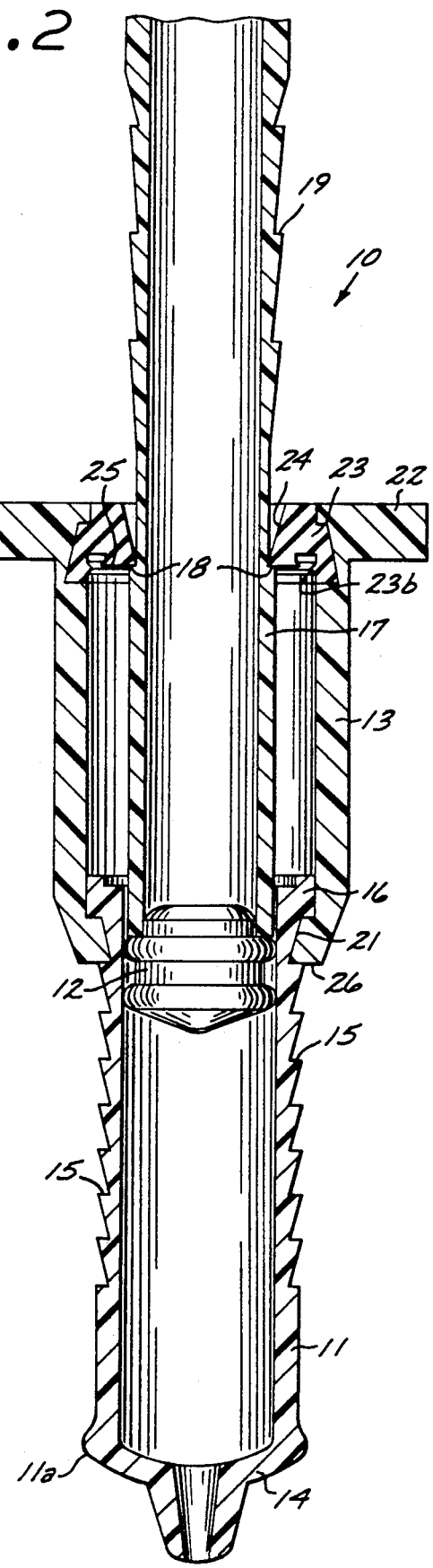

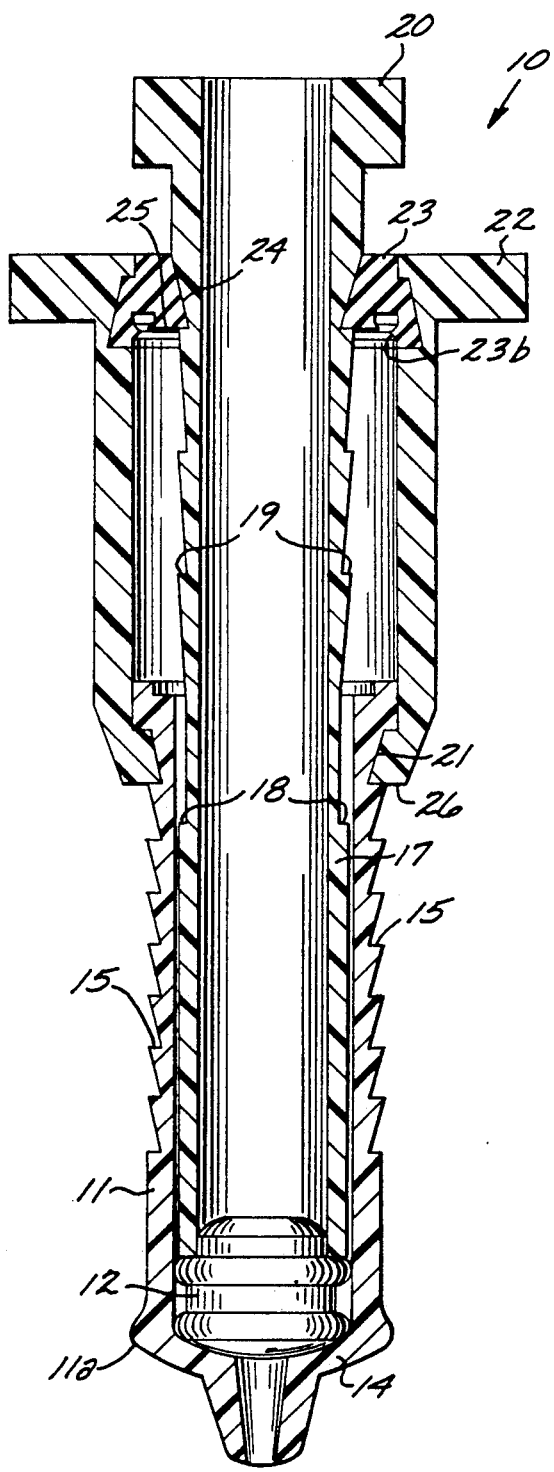
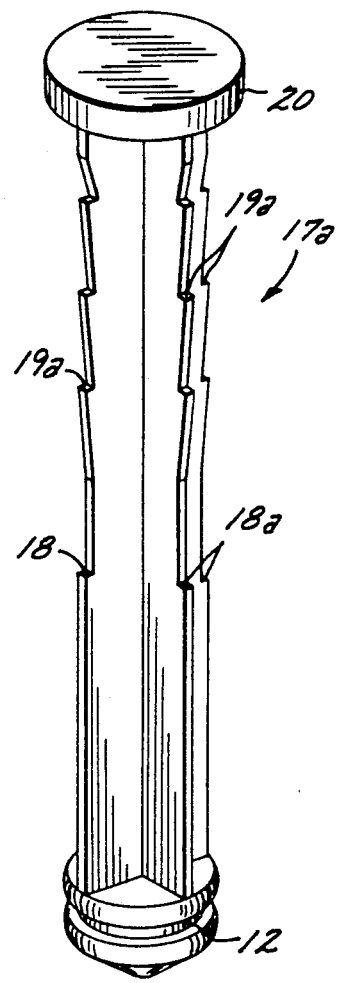
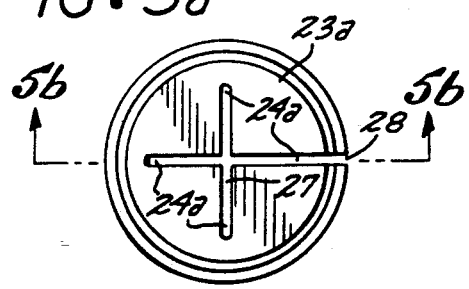
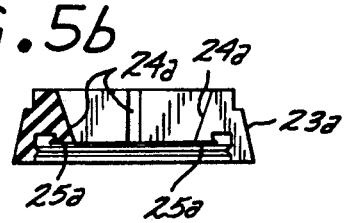

SELF-LOCKING SINGLE-USE SYRINGE

BACKGROUND OF THE INVENTION

1. Field of the Invention

This invention generally relates to syringes and more particularly pertains to syringes which cannot be reused.

2. Brief Description of the Prior Art

In the usual practice, non-reuse of the single-use type syringe is left to the good will of the users. In recent times however the requirement to prevent actual reuse has become more acute as the practice, customary in environments like that of drug addicts, has become very risky due to the spread of infectious diseases.

Several types of technical measures have thus been proposed to make self-locking syringes non-reusable after a first use. The solutions proposed by the known art however display technical features which make said syringes complicated and costly to produce as well as often difficult for the user to handle and unsatisfactory in operation. For example there have been proposed syringes wherein the cylindrical body which receives the liquid is internally equipped with stops for locking the thrust piston once it has reached complete insertion condition after injection of the liquid taken in. The presence of said stops on the sliding walls of the piston seal has however various drawbacks, a general loss of seal between the piston and the syringe body being of primary concern. (see for example U.S. Pat. No. 4,995,869) In addition it is always preferable that the part of the syringe which receives the liquid to be injected be as smooth as possible and free of roughness.

The general purpose of the present invention is to overcome the above mentioned drawbacks by offering a self-locking single-use syringe with provisions which would prevent reuse thereof and would also be simple and economical to produce as well as easy for the user to use, at the same time providing a receiving part for the liquid to be injected substantially similar to that of a normal syringe.

SUMMARY OF THE INVENTION

In view of said purpose there has been realized a syringe comprising a hollow cylindrical body having a bottom closing part bearing a connecting joint for connection of a needle thereto and in which there moves in a sliding and sealed manner a piston driven by a stem, the syringe being characterized in that it includes a sliding sleeve on the outside of the body. A first unidirectional engagement means between the body and sleeve prevents the movement of the sleeve towards the bottom closing part and second unidirectional engagement means between said sleeve and said stem prevents withdrawal of the stem relative the sleeve.

To further clarify the explanation of the innovative principles of the present invention and its advantages as compared with the known art there is described below with the aid of the annexed drawings a preferred embodiment by way of nonlimiting example in accordance with said principles.

BRIEF DESCRIPTION OF THE DRAWINGS

FIG. 1 shows a cross sectional view of the syringe in accordance with the present invention in an initial condition;

FIG. 2 shows the syringe of FIG. 1 with the piston entirely retracted; and

FIG. 3 shows the syringe of FIG. 1 with the piston at end of travel after use by the user;

FIG. 4 is a perspective view of the stem portion of an alternative embodiment; and FIGS. 5a and 5b are a top plan view and a cross-sectional view of the engagement element for use with the stem shown in FIG. 4.

DETAILED DESCRIPTION OF THE PREFERRED EMBODIMENT

With reference to FIG. 1 a syringe in accordance with the present invention, indicated generally by reference number 10, comprises a hollow body 11, a piston 12 driven by a stem 17 and an outer sleeve 13.

The hollow body 11 is cylindrical internally and is closed at one end by a drilled bottom part 14 terminating with a connecting joint for engagement of a hollow needle of the known art (not shown). A circumferential bulge 11a is formed on the hollow body's exterior surface near its bottom part 14. Said body 11 is provided externally, at least in its upper part, with a series of circumferential steps 15 tapered toward the bottom part 14 and ends with an edge 16 formed in such a manner as to constitute an engagement element with the sleeve 13 as explained below.

In the body 11 is received in a sliding manner said piston 12 of yielding material, such as for example rubber, fixed to the stem 17 with any known method for this specific construction detail. On the outer surface of the drive stem 17 of the piston 12 there is a ledge 18 inside the syringe body, and in the tail part, a series of circumferential steps 19 tapered toward the piston end of the stem 17 and terminating near the thrust end 20. The sleeve 13 has its lower part ending with an internal annular shoulder 21 sufficiently elastic to slide in one direction on the circumferential steps 15 of the hollow body 11 and engage thereon in the opposite direction with a ledge surface 26 extending outside the body 11 for a length substantially equal to the length of the portion of the body having the steps 15.

The sleeve 13 ends at the top with a gripping flange 22. In the upper internal part of the sleeve 13 and substantially level with the flange 22 there is a circular engagement element 23 integral with said sleeve. Said element 23 is advantageously formed with lip structure 23b to receive and engage in a yielding manner with the edge 16 of the body 11. In addition, in its internal part element 23 is equipped with a shoulder 24 capable of sliding one way on the circumferential steps 19 of the piston and engage thereon in the opposite direction with a ledge surface 25. The surface 25 constitutes in addition a stop for the ledge 18 of the stem 17.

In this alternative embodiment illustrated in FIG. 4, the drive stem 19a is shaped in an X-configuration when viewed in cross-section. A series of steps 19a are formed on the ends of the X, each step being tapered toward the piston end of stem 17a. In the alternative embodiment, engagement element 23a comprises a disc having an X-shaped opening 27 extending therethrough. The disc 23a is split at 28 to facilitate assembly and includes shoulders 24a for engagement with steps 19a.

Operation of the syringe in accordance with the present invention is as follows. The syringe is presented to the user ready for use in the configuration illustrated in FIG. 1. To intake the liquid to be injected, the piston 12 is then retracted by pulling with sufficient force to free the end 16 from the seat of the ring 23. Bulge 11a facilitates the holding of syringe 10 for this purpose. During the intake movement the ledge 18 of the stem 17 engages with the shoulder 24 of the engagement element 23 integral with the sleeve 13. Proceeding in its intake movement the stem 17 is thus capable of pulling the sleeve 13 whose shoulder 21 slides trippingly along the tapered parts of the steps 15 of the body 11 until it engages finally in the last of said steps and assumes the configuration illustrated in FIG. 2. The distance between ledge 18 and surface 25 as shown in FIG. 1 as well as the distance between ledge 18 and first step 19 as shown in FIG. 2 are intended to provide some play at the beginning and end of the intake stroke so that air can readily be expelled and vein location can be confirmed.

In the course of the subsequent movement of lowering of the piston 12 to inject the intake liquid, the sleeve 13 is thus engaged in the last of the steps 15 reached and therefore cannot slide to receive the body 11 again. In this manner the tapered parts of the circumferential steps 19 of the stem 17 slide on the shoulder 24 until the piston 12 reaches its end of stroke position as shown in the configuration of FIG. 3 at the end of movement of injection of the liquid from the syringe body. In said configuration the steps 15 and the shoulder 21 prevent sliding of the sleeve 13 on the body 11 and also the steps 19 and the ledge 25 prevent sliding and withdrawal of the piston 12 from the body 11. It is thus impossible to reuse the syringe.

The alternative embodiment syringe is intended for smaller capacities such as for example a 1 ml size used for insulin injections and functions in an identical manner. The piston 12 is retracted from within body 11 by pulling on stem 17a such that ledges 18a engage element 23a and cause sleeve 13 to trippingly slide over tapered steps 15. Upon retraction, piston 12 is then pushed back into body 11 as the stepped edges 19a of the "X" trippingly slide over shoulders 24a of engagement element 23a. Once fully compressed, positive engagement of the last of steps 19a with the four ledges 25a of disc, 23a as well as the last of steps 15 with shoulder 26 prevents syringe 10 from being reused.

Of course the dimensions and the number of the circumferential steps or the body 11 and the stem 17 can be varied depending on the degree of seal it is intended to obtain. For example, the stem 17 which controls the piston 12 instead of having a diameter slightly smaller than that of the body could have a smaller diameter and in this case the annular element 23 would have a corresponding limited central hole. Solutions could also be provided with a limited number of steps on the body and the piston stem, even a single end of stroke step for both.

In addition the steps 15 and 19 could extend entirely around the circumference of the respective elements, as is clear to those skilled in the art, just as the cross section of the outer wall of the syringe body or of the stem 17 could be other than circular, the surfaces of the sleeve which couple with them being correspondingly formed. Finally, the initial removable engagement between the end 16 and the ring 23, which is useful to prevent accidental operation of the syringe, could of course be omitted or replaced by various safety devices such as for example removable couplings or parts in other positions.

Although the invention has been described for a specific embodiment it is evident that many alternatives and variations, such as in materials and dimensions, will be apparent to those skilled in the art in light of the foregoing description. Accordingly, the invention is intended to embrace all of the alternatives and variations that fall within the spirit and scope of the invention.

What is claimed is:

1. A mono-use syringe, comprising:
   a hollow elongated body having a distal end configured for interconnection to a hollow needle;
   a stem driven piston, slidingly translatable within said body and oriented such that the stem protrudes from the proximal end of said hollow body;
   a sleeve member fitted about said elongated body's exterior and having a proximal end configured to receive said stem therethrough;
   a first unidirectional engagement means operative to allow said sleeve member to be drawn away from said hollow body's distal end and prevent its movement towards the distal end; and
   a second unidirectional engagement means operative to allow said stem to be pushed through said sleeve member's proximal end towards said hollow body's distal end and prevent movement in the opposite direction whereby the syringe is rendered unusable after a single use.

2. The syringe of claim 1 wherein said first unidirectional engagement means is formed on said hollow body's exterior.

3. The syringe of claim 2 wherein said first unidirectional engagement means comprises circumferential steps formed on said hollow body's exterior, said steps being tapered towards said body's distal end.

4. The syringe of claim 3 wherein said circumferential steps extend completely around the circumference of said hollow body's exterior.

5. The syringe of claim 1 wherein said second unidirectional engagement means are formed on said stem's exterior.

6. The syringe of claim 5 wherein said second unidirectional engagement means comprises circumferential steps formed on said stem's exterior, said steps being tapered towards the piston.

7. The syringe of claim 6 wherein said circumferential steps extend completely around the circumference of said stem.

8. The syringe of claim 6 wherein said stem is X-shaped in cross-section and wherein said second unidirectional engagement means comprises circumferentially oriented steps formed on the ends of the "X".

9. The syringe of claim 1 wherein a ledge is formed on the exterior surface of said stem configured to engage said proximal end of said sleeve and pull the sleeve away from said hollow body's distal end as the stem driven piston is withdrawn therefrom.

10. The syringe of claim 1 further comprising a locking means for maintaining said syringe in a ready to use configuration, said locking means being easily overcome upon application of force as the stem driven piston is initially withdrawn.

11. The syringe of claim 10 wherein said locking means are formed in the proximal end of said sleeve member.

12. The syringe of claim 2 wherein said sleeve member extends along the exterior of said hollow body for a length substantially equivalent to the length of said first unidirectional engagement means.

* * * * *